(12) United States Patent
Sella

(10) Patent No.: US 9,940,822 B2
(45) Date of Patent: Apr. 10, 2018

(54) SYSTEMS AND METHODS FOR ANALYSIS OF SUBJECT ACTIVITY

(71) Applicant: Kytera Technologies Ltd., Yokneam Ilit (IL)

(72) Inventor: Assaf Sella, Rishpon (IL)

(73) Assignee: Kytera Technologies Ltd., Yokneam Illit (IL)

( * ) Notice: Subject to any disclaimer, the term of this patent is extended or adjusted under 35 U.S.C. 154(b) by 0 days.

(21) Appl. No.: 15/039,424

(22) PCT Filed: Nov. 26, 2014

(86) PCT No.: PCT/IL2014/051022
§ 371 (c)(1),
(2) Date: May 26, 2016

(87) PCT Pub. No.: WO2015/079436
PCT Pub. Date: Jun. 4, 2015

(65) Prior Publication Data
US 2016/0379476 A1 Dec. 29, 2016

Related U.S. Application Data

(60) Provisional application No. 61/908,767, filed on Nov. 26, 2013, provisional application No. 61/910,362, filed on Dec. 1, 2013.

(51) Int. Cl.
*G08B 1/08* (2006.01)
*G08B 25/01* (2006.01)
(Continued)

(52) U.S. Cl.
CPC ......... *G08B 25/016* (2013.01); *A61B 5/002* (2013.01); *A61B 5/1113* (2013.01); *A61B 5/746* (2013.01);
(Continued)

(58) Field of Classification Search
CPC combination set(s) only.
See application file for complete search history.

(56) References Cited

U.S. PATENT DOCUMENTS 9,257,029 B1 * 2/2016 Hendrick, III ..... G08B 21/0415
9,361,778 B1 * 6/2016 German ............ G08B 21/0423
(Continued)

FOREIGN PATENT DOCUMENTS

CN 101520502 9/2009
CN 103338511 10/2013
(Continued)

OTHER PUBLICATIONS

International Preliminary Report on Patentability dated Jun. 9, 2016 From the International Bureau of WIPO Re. Application No. PCT/IL2014/051022.
(Continued)

*Primary Examiner* — Travis Hunnings

(57) ABSTRACT

There is provided a method of detection and monitoring of at least one position based activity by a subject, comprising: providing a wearable monitoring device including at least one position tag for tracking location of the subject in a space; collecting body movement and location data of the subject within the space based on the tracked location of the position tag; providing at least one activity sensor configured to sense at least one body movement of the subject within the space; collecting body movement data based on the activity sensor; correlating the body movement data with the location data; contextually analyzing the correlation to identify at least one abnormal event or at least one normal event based on subject body movement and location where the body movement is performed; and generating an alert indicative of the abnormal event or the normal event.

16 Claims, 7 Drawing Sheets

(51) Int. Cl.
  *G08B 21/04* (2006.01)
  *A61B 5/00* (2006.01)
  *A61B 5/11* (2006.01)
  *H04L 29/06* (2006.01)
  *H04L 29/08* (2006.01)
  *H04W 4/02* (2018.01)

(52) U.S. Cl.
  CPC ....... *G08B 21/043* (2013.01); *G08B 21/0423* (2013.01); *G08B 21/0446* (2013.01); *G08B 21/0453* (2013.01); *G08B 21/0492* (2013.01); *A61B 5/1117* (2013.01); *A61B 5/1118* (2013.01); *A61B 2505/07* (2013.01); *H04L 65/102* (2013.01); *H04L 67/18* (2013.01); *H04L 67/42* (2013.01); *H04W 4/025* (2013.01)

(56) References Cited

U.S. PATENT DOCUMENTS

| | | | |
|---|---|---|---|
| 9,501,613 B1* | 11/2016 | Hanson | G06F 19/00 |
| 2007/0288263 A1 | 12/2007 | Rodgers | |
| 2008/0001735 A1* | 1/2008 | Tran | G06F 19/3418 340/539.22 |
| 2008/0021731 A1 | 1/2008 | Rodgers | |
| 2009/0174546 A1 | 7/2009 | Lian et al. | |
| 2010/0274100 A1 | 10/2010 | Behar et al. | |
| 2011/0010093 A1 | 1/2011 | Partridge et al. | |
| 2013/0010617 A1 | 1/2013 | Chen et al. | |
| 2013/0060167 A1 | 3/2013 | Dracup et al. | |
| 2013/0225200 A1 | 8/2013 | Hamida et al. | |
| 2016/0377697 A1 | 12/2016 | Sella | |

FOREIGN PATENT DOCUMENTS

| | | |
|---|---|---|
| CN | 103401922 | 11/2013 |
| EP | 1071055 | 1/2001 |
| EP | 1617601 | 1/2006 |
| WO | WO 2007/093404 | 8/2007 |
| WO | WO 2011/056218 | 5/2011 |
| WO | WO 2015/079436 | 6/2015 |
| WO | WO 2015/079437 | 6/2015 |

OTHER PUBLICATIONS

International Preliminary Report on Patentability dated Jun. 9, 2016 From the International Bureau of WIPO Re. Application No. PCT/IL2014/051023.
International Search Report and the Written Opinion dated Mar. 2, 2015 From the International Searching Authority Re. Application No. PCT/IL2014/051023.
International Search Report and the Written Opinion dated Mar. 5, 2015 From the International Searching Authority Re. Application No. PCT/IL2014/051022.
Supplementary European Search Report and the European Search Opinion dated Jul. 6, 2017 From the European Patent Office Re. Application No. 14865972.5. (8 Pages).
Supplementary European Search Report and the European Search Opinion dated Jun. 21, 2017 From the European Patent Office Re. Application No. 14865208.4. (9 Pages).
Bal et al. "Localization in Cooperative Wireless Sensor Networks: A Review", Proceedings of the 2009 13th Interantional Conference on Computer Supported Cooperative Work in Design, XP031460849, Santiago de Chile, Chile, Apr. 22-24, 2009, p. 438-443, Apr. 22, 2009.

* cited by examiner

SYSTEMS AND METHODS FOR ANALYSIS OF SUBJECT ACTIVITY

RELATED APPLICATIONS

This application is a National Phase of PCT Patent Application No. PCT/IL2014/051022 having International filing date of Nov. 26, 2014, which claims the benefit of priority under 35 USC § 119(e) of U.S. Provisional Patent Application Nos. 61/908,767 filed on Nov. 26, 2013 and 61/910,362 filed on Dec. 1, 2013. The contents of the above applications are all incorporated by reference as if fully set forth herein in their entirety.

BACKGROUND

The present invention, in some embodiments thereof, relates to systems and methods for analysis of activities of a subject and, more specifically, but not exclusively, to systems and methods for determining an abnormal event of a subject based on activity analysis.

Certain populations living at home are at increased risk of harm, for example, the elderly, the disabled, and people with chronic medical conditions. Such subjects would like to live at home (e.g., to remain independent, and/or to remain within familiar surroundings), but may require help at certain times, for example, when feeling unwell, when needing extra help to perform certain home activities, and when medical symptoms arise. The subjects may be living alone, and when a problem arises would otherwise remain helpless.

Different systems such as Personal Emergency Response Systems (PERS) have been developed to address the needs of this population. In one example, subjects are provided with a wearable button, that when pushed, provides a notification to a monitoring center that help is needed.

SUMMARY

According to an aspect of some embodiments of the present invention there is provided a computerized method of detection and monitoring of at least one position based activity by a subject, comprising: providing a wearable monitoring device including at least one position tag configured to communicate with anchor devices, each device including at least one sensor configured for tracking location of the position tag in a space, the wearable monitoring device further configured to be detachable and wearable on a subject; collecting body movement and location data of the subject within the space based on the tracked location of the at least one position tag; providing at least one activity sensor configured to sense at least one body movement of the subject within the space, wherein the wearable monitoring device includes the at least one activity sensor; collecting body movement data based on the at least one activity sensor; correlating the body movement data with the location data; contextually analyzing the correlation to identify at least one abnormal event or at least one normal event based on subject body movement and location where the body movement is performed; and generating an alert indicative of the at least one abnormal event or the at least one normal event.

Optionally, the method further comprises collecting postural data based on the at least one activity sensor; wherein correlating comprises correlating the postural data with the body movement and location data; and wherein contextually analyzing comprises contextually analyzing the correlation to identify at least one abnormal event or at least one normal event based on subject body movement and location where the postural data is performed.

Optionally, the method further comprises collecting gesture data based on the at least one activity sensor; wherein correlating comprises correlating the gesture data with the body movement and location data; and wherein contextually analyzing comprises contextually analyzing the correlation to identify at least one abnormal event or at least one normal event based on subject body movement and location where the gesture data is performed. Optionally, the gesture data includes data indicative of at least one of movement of one or more limbs, and rotational motion of the subject.

Optionally, the method further comprises providing at least one physiological sensor configured to sense at least one physiological parameter of the subject within the space, wherein the wearable monitoring device includes the at least one physiological sensor; collecting the at least one physiological parameter based on the at least one physiological sensor; and wherein correlating comprises at least one of correlating the at least one physiological parameter with the body movement and location data; wherein contextually analyzing comprises contextually analyzing the correlation to identify at least one abnormal event or at least one normal event based on subject body movement and location where the at least one physiological parameter is measured.

Optionally, contextually analyzing comprises contextually analyzing the correlation based on the correlation in view of at least one contextual data member selected from the group consisting of: day of the week, time of day, temperature in the space, amount of light in the space, proximity data, presence of other people in proximity to the subject, subject medication compliance, and subject movement and location relative to objects within the space.

Optionally, contextually analyzing comprises contextually analyzing the correlation based on a learned routine data set storing at least one normal routine of the subject to identify the at least one abnormal event.

Optionally, the method further comprises generating the learned routine data set based on learning at least one normal routine of the subject based on a pattern of at least one of the tracked location, body movement, posture, at least one gesture, and physiological parameters.

Optionally, the learned routine data set includes at least one normal routine learned from different subjects.

Optionally, the at least one abnormal event is selected from the group consisting of: a deviation from the normal routine, a distress situation, and a deviation from an activity trend.

Optionally, the at least one abnormal event is selected from the group consisting of: a fall, a crawl, abnormal gait, and restless movement disorder.

Optionally, contextually analyzing comprises contextually analyzing the correlation to identify at least one activity of daily living, and analyzing the at least one activity of daily living to identify the at least one abnormal event related to the at least one activity of daily living.

Optionally, the method further comprises identifying at least one activity of the subject based on a location and a trajectory of the subject calculated based on the tracked location, relative to predetermined locations of at least one object within a space of the subject, wherein the at least one object is associated with the at least one activity.

Optionally, the predetermined locations of the at least one object within the space are determined based on at least one member of the group consisting of: tagging each respective object during an installation process; based on a floor plan of the space of the subject; and based on a self-constructed floor plan.

Optionally, the method further comprises comparing the trajectory of the subject relative to the at least one object, to at least one trajectory of other subjects relative to other objects similar to the at least one object.

Optionally, contextually analyzing further comprises contextually analyzing the correlation to identify at least one abnormal event, based on a correlation of a current trajectory of the subject to at least one of: past trajectories of the subject and trajectories of other subjects, to identify an abnormal trajectory of the subject, the abnormal trajectory associated with the at least one abnormal event, wherein the correlation of the current trajectory is performed based on the position data, to correlate same or similar locations of the trajectory.

Optionally, the anchor devices are set to be detachably deployed in locations in a space, and further comprising calculating locations of the anchor devices by: capturing by the anchor devices relative distance indication messages transmitted from the anchor devices; calculating, based on each of the relative distance indication message, distance indicative parameters indicative of a distance between a pair of anchor devices from the anchor devices; aggregating the distance indicative parameters; and calculating a dataset which maps a location of each one of the anchor devices in the space according to the aggregated distance indicative parameters.

Optionally, the anchor devices are set to be detachably deployed in locations in a space, and further comprising: capturing a finger-print set of RF signatures of a place in the space, the RF signatures communicated between the wearable monitoring device and at least one of the anchor devices; receiving messages communicated between the wearable monitoring device and at least one of the anchor devices; and calculating an estimated location of the wearable monitoring device by comparing the messages to the finger-print set.

Optionally, the method further comprises activating an audio monitor for communication between the subject and a caregiver based on the identification of the at least one abnormal event.

According to an aspect of some embodiments of the present invention there is provided a system for detection and monitoring of at least one position based activity by a subject, comprising: a wearable monitoring device configured to be detachable and wearable on a subject, comprising: at least one position tag configured to communicate with anchor devices, each device including at least one sensor configured for tracking location of the at least one position tag in a space; and at least one activity sensor configured to sense at least one body movement of the subject within the space; and a remote monitoring server configured to: receive body movement and location data of the subject within the space; generate, based on a contextual analysis of a correlation of the body movement with the location data, a message indicative of at least one abnormal event or at least one normal event.

Optionally, the at least one activity sensor is further configured to sense at least one of: at least one gesture and at least one postural data of the subject within the space; and the remote monitoring server is further configured to receive at least one of the at least one gesture and the at least one postural change; and generate, based on a contextual analysis of a correlation of the body movement and the location with at least one of the at least one gesture and the at least one postural change, a message indicative of at least one abnormal event or at least one normal event.

Optionally, the wearable monitoring device further includes at least one physiological sensor configured to sense at least one physiological parameter of the subject within the space; and the remote monitoring server is further configured to receive the at least one physiological parameter; and generate, based on a contextual analysis of a correlation of the body movement and location data with the at least one physiological parameter, a message indicative of at least one abnormal event or at least one normal event.

Optionally, the at least one physiological sensor is selected from the group consisting of: a heart rate sensor, a heart rate variability sensor, an oxygen saturation sensor, a respiratory rate sensor, and a skin temperature sensor.

Optionally, the system further comprises activating the at least one physiological sensor based on identification of the at least one abnormal event, to confirm or retract the at least one abnormal event, to reduce overall power consumption.

Optionally, the system further comprises an activity database, the activity database storing learned data representing combinations of tracked subject location data correlated with subject body movement data and/or gesture data and/or physiological data representing different activities, wherein the activity database is in communication with the remote monitoring server, and the remote monitoring server uses the activity database to identify the at least one abnormal event. Optionally, the data within the activity database is collected based on one or more members of the group consisting of: past data of the same subject, data from other similar subjects, data from other similar subjects having similar medical conditions as the subject.

Optionally, the position tag is active, being configured to periodically transmit at least one distance indication message for receipt and processing by at least one of the anchor devices, to determine the location of the position tag relative to the anchor devices. Alternatively or additionally, the position tag is passive, being configured to receive distance indication messages transmitted by the anchor devices, the position tag further configured to process the received message, to determine the location of the position tag relative to the anchor devices.

Optionally, the anchor devices are set to be detachably deployed in locations in a space, and further comprising an RF location module configured to: receive a finger-print set of RF signatures of a place in the space, the RF signatures communicated between the wearable monitoring device and at least one of the anchor devices; receive messages communicated between the wearable monitoring device and at least one of the anchor devices; calculate an estimated location of the wearable monitoring device by comparing the messages to the finger-print set; and provide the estimated location of the wearable monitoring device.

Optionally, the wearable monitoring device is designed as a wristband, including the position tag and the at least one activity sensor integrated therein.

Optionally, the wearable monitoring device further includes a panic button configured to be reversible attached to the subject and when pressed to generate an alert to a care giver by triggering a local monitoring unit.

Optionally, the wearable monitoring device further includes a wireless communication module configured to communicate with a local monitoring unit communicating with the remote monitoring server.

Optionally, the wearable monitoring device further includes a microphone and a speaker configured to enable two-way voice communication with a caregiver.

Optionally, the wearable monitoring device further includes a global position element configured to generate a global location of the data representing at least one tracked location of the subject when the subject is located out of range of the anchor devices.

Optionally, the system further comprises a local monitoring unit configured to receive data representing the location of the wearable monitoring device from the anchor devices, calculate the location of the wearable monitoring device, and transmit the calculated location to the remote monitoring server.

Optionally, the remote monitoring server is further configured to detect a fall based on the location and body movement, and analyze the fall based on the body movements relative to predefined objects within the space, to increase the reliability of detection of the fall based on identifying falls in context within the space where falls are more likely to occur. Optionally, the remote monitoring server is further configured to receive at least one of normal routine information of the subject and a time of day, and analyze the fall based on the at least one of normal routine information and the time of day to increase the reliability of detection of the fall based on at least one of abnormal routine of the subject and subject activity during abnormal times of the day.

Optionally, the at least one activity sensor is selected from the group consisting of: an accelerometer configured to measure linear acceleration, and a gyroscope configured to measure angular acceleration.

Optionally, the remote monitoring server is further configured to dynamically control activation of at least one activity sensor of the wearable device when the subject is identified as being located in proximity to one or more predefined objects in the space, and/or to dynamically control activation of at least one position tag when the subject is identified as performing a significant gesture and/or body movement, to reduce overall power consumption.

According to an aspect of some embodiments of the present invention there is provided a computerized method of detection and monitoring of care provided by a caregiver to a subject, comprising: providing a wearable monitoring device including at least one position tag to a caregiver, and another wearable monitoring device including at least one position tag to a subject, the at least one position tag configured to communicate with anchor devices, each device including at least one sensor for tracking location of the position tag in a space, each wearable monitoring device further configured to be detachable and wearable on the caregiver and on the subject being cared for by the caregiver; calculating a quality of care dataset based on the relative tracked locations of the at least one position tag of the subject relative to the at least one position tag of the caregiver; analyzing the quality of care dataset to identify at least one abnormal event in care provided to the subject by the caregiver; and generating an alert indicative of the at least one abnormal event.

Optionally, the quality of care data set includes at least one quality of care metric calculated based on one or more members of the group consisting of: an average of a distance between the caregiver and the subject as a function of time, a maximal of the distance, and a function of the distance over time.

Optionally, analyzing further comprising analyzing the quality of care dataset based on a location context of the subject and the caregiver based on body movements detected by respective position tags.

Optionally, the method further comprises providing at least one activity sensor to the caregiver and to the subject, the at least one activity sensor configured to sense at least one of a posture and a gesture of the caregiver and at least one of a posture and a gesture of the subject; identifying at least one of a sequence of gestures and a sequence of postures of at least one of the caregiver and the subject representing good care or bad care; and calculating the quality of care dataset based on the sequence of gestures.

Optionally, identifying at least one of the sequence of gestures and sequence of postures is based on machine learning including training data gathered from the same caregiver and/or different caregivers performing pre-defined good care or bad care on the same subject and/or different subjects.

Optionally, the quality of care dataset is calculated based on an analysis of voice data generated by the subject calling the caregiver, and the responsiveness of the caregiver to the calling subject associated with changes in the relative locations of the at least one position tag of the subject relative to the at least one position tag of the caregiver. Optionally, the quality of care dataset is calculated based on the responsiveness of the caregiver measured by at least one member of the group consisting of: average response time, maximal response time, predefined deviation from average response time, and response time in relation to a time of day.

Optionally, the method further comprises automatically learning the name of the caregiver by analyzing voice data of the subject and the responsiveness of the caregiver, wherein the quality of care is calculated when the subject calls the name of the caregiver.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1A:
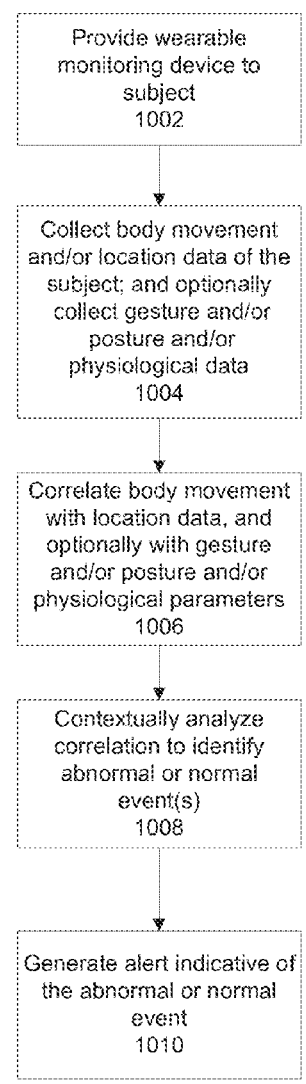
FIG. 1A is a flowchart of a computerized method for detection and monitoring of contextually analyzed activities of a subject, in accordance with some embodiments of the present invention.

The present invention, in some embodiments thereof, relates to systems and methods for analysis of activities of a subject and, more specifically, but not exclusively, to systems and methods for determining an abnormal event of a subject based on activity analysis.

An aspect of some embodiments of the present invention relates to systems and/or methods for detection of one or more abnormal events associated with a subject within a certain space based on contextual analysis of individual body movement correlated with location data. Alternatively or additionally, detection of one or more abnormal events associated with the subject within the certain space is based on contextual analysis of limb gesture and/or posture and/or physiological data correlated with individual body movement and location data. The individual body movement and location data of the subject is detected based on an analysis of sensor data mapping motion of the subject during a monitoring period, for example, where the subject is currently located within a home, and/or patterns of location of the subject relative to identified and mapped objects (e.g., sofa, refrigerator, desk) in the home and/or relative to identified and mapped places in the home at its vicinity (e.g., by a location system that provides room-level location information such as being in the bedroom, hallway, kitchen, backyard, and the like). By contextually analyzing as above, the systems and/or methods improve the accuracy of detection of abnormal events, such as a fall, restless movement syndrome, and disorientation. In certain cases, the analysis of the correlation detects abnormal events that would otherwise be determined to be normal when analyzed without the correlated data (i.e., reduces false negatives). In other cases, the analysis of the correlation identifies events as being normal, when the events would otherwise be determined to be abnormal when analyzed without the correlated data (i.e., reduces false positive). For example, certain limb motions are determined to be normal when occurring near the fridge (e.g., opening of the fridge door and removal of food), and represent an abnormal event when occurring in a different context (e.g., the middle of a living room). The gesture of one or more limbs may be associated with a certain posture. For example, hands located for long periods of time at knee level suggest the subject is abnormally bending over, such as due to sudden back pain.

Alternatively or additionally, measured physiological parameters of the subject (e.g., vital signs) are correlated with body movement and/or location data of the subject to determine whether the abnormal event or normal event is occurring. For example, an increase in body temperature and/or heart rate is determined to be normal when the subject is identified as exercising on a stationary home exercise bike, and represent the abnormal event when the subject is identified as lying on the living room floor.

Optionally, the contextual analysis is performed in view of additional contextual data, to identify whether the correlated data represents the normal or abnormal event. The contextual data may include, for example, one or more of: day of the week, time of day, amount of light in the room, room temperature, proximity data, presence of other people in proximity to the subject, subject medication compliance, and subject body movement and/or location relative to objects within the space. For example, limb movement gestures and/or postural changes performed by the subject when in the living room after the subject takes medications may identify the abnormal event (e.g., adverse effects of the medication), whereas the same limb movement gestures in the same living room without the medication may represent the normal event (e.g., subject dancing). For example, tracked body movement of the subject to the living room to start sewing gestured during the day may represent the normal event, whereas the same body movements and gestures in the middle of the night may represent the abnormal event (e.g., subject sleepwalking, confusion, or delusion).

Optionally, a wearable monitoring device includes one or more sensors to track the location of the subject, measure postures, measure gestures, and/or measure one or more physiological parameters. The wearable monitoring device is designed to be detachable and wearable by the subject, for example, as a bracelet.

Optionally, the systems and/or methods learn normal activity of the subject, for example, based on one or more machine learning methods. The correlated data is compared to the learned data set to determine whether the correlation represents normal activity or the abnormal event. Learning may include learning normal activity and/or abnormal events from other similar subjects.

An aspect of some embodiments of the present invention relates to systems and/or methods for monitoring quality of care received by a subject from a caregiver. The quality of care is monitored based on at least one calculated quality of care dataset such as a metric. The dataset may be calculated from data representing relative tracked movements of the subject relative to the caregiver. The quality of the dataset is analyzed to identify whether the care being provided is of suitable quality, and/or whether one or more abnormal events are occurring.

The quality of care dataset may be calculated from tracking data collected from wearable monitoring devices (e.g., as described herein) worn by the subject and the caregiver. The quality of care metric may be based on location, for example, closer distances expected in the kitchen (e.g., to help in eating) and further distances expected when outside.

Optionally, the quality of care dataset is based on a sequence of gestures and/or body movements and/or postural changes performed by the subject and/or the caregiver within the subject location, for example, a pattern of gestures indicating the caregiver assisting the subject with dressing is designated as normal when occurring inside the bedroom, and designated as abnormal when occurring in the kitchen.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1B:
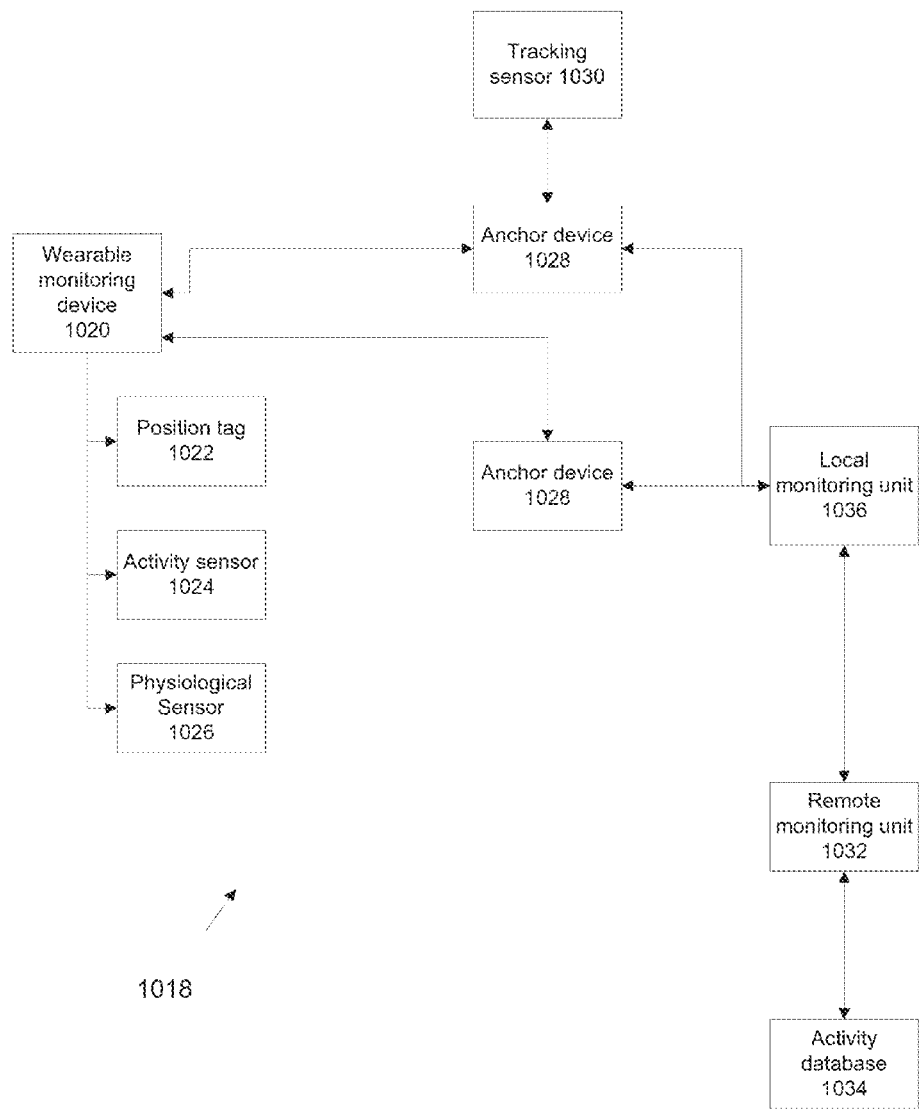
FIG. 1B is a block diagram of a system for detection and monitoring of contextually analyzed activities of a subject, in accordance with some embodiments of the present invention.

Reference is now made to FIG. 1A, which is a flowchart of a computer implemented method for detection and monitoring of one or more contextually analyzed activities of a subject, in accordance with some embodiments of the present invention. The method determines whether the subject activity is an abnormal event, by contextually analyzing the subject location correlated with body movement, and optionally correlated with additional data such as posture and/or gesture and/or physiological data. Reference is also made to FIG. 1B which is a block diagram of a system 1018 for detection and monitoring of one or more position based activities of the subject, in accordance with some embodiments of the present invention. The method of FIG. 1A may be executed based on the system of FIG. 1B.

The systems and/or methods described herein identify normal or abnormal events mainly based on the wearable monitoring device, reducing the cost and/or need for additional dedicated sensors. Many events may be detected based on the same wearable monitoring device, instead of requiring one or more dedicated sensors to detect each activity. For example, a motion sensor to detect entrance to a room is not needed, as instead, the systems and/or methods detect room entrance based on tracking location of the wearable device. In another example, a door sensor to detect opening of the refrigerator is not needed, as instead, the systems and/or methods detect location and/or gestures of the subject near the fridge and/or opening of the door.

As described herein, the term body movement data means the distinction between a static state (i.e., no movement), and a non-static state (i.e. movement of a limb and/or movement of the subject). Body movement information may be received based on tracking the location of the subject (e.g. no change in location represents the static state), and/or based on activity and/or movement sensors monitoring the subject (e.g., accelerometer).

Consideration of posture, gesture and/or physiological data in addition to tracked location and body movement sensor data improves accuracy of abnormal event detection, for example, by reducing the probability of a false alert, and/or reducing the probability of incorrect event identification. For example, the contextual analysis of accelerometer based data correlated with subject location data improves accuracy of a fall event. For example, when the accelerometer data is associated with a fall, but the corresponding location data represents a location where the subject is normally stationary (e.g. on a sofa), a false alarm is avoided by identifying the fall gesture as a normal sitting on the sofa event. In another example, when the gesture data represents the subject falling gracefully such that the accelerometer does not detect a fall, but the subject location is associated with a location where normally the subject moves faster, a fall event is identified. Relying on the accelerometer data alone in such a case would miss the fall event.

At 1002, a subject located with a space, for example, a home environment, a rehabilitation facility, and a retirement home, is provided with a wearable monitoring device 1020. Wearable monitoring device 1020 is designed to be detachable and wearable by the subject, for example, a bracelet, a necklace, a hat, a shirt, and a belt. Wearable monitoring device may be designed as a single unit, integrating one or more sensors described herein into the single component. The single unit wearable design allows for easy application and removal, while being minimally or non-intrusive to the subject.

Wearable monitoring device 1020 includes one or more position tags 1022 that track location of the respective tag in the space. Optionally, position tag 1022 is designed for integration with a subject tracking and/or position system, for example, as described with reference to United Stated Provisional Patent Application No. 61/908,767, filed Dec. 26, 2013, titled "DEPLOYABLE MONITORING SYSTEM AND METHODS OF USING THEREOF", by the same inventor of the present application, incorporated herein by reference in its entirety. Optionally, position tag 1022 wirelessly communicates with multiple anchor devices 1028. Each device 1028 includes one or more tracking sensors 1030 for tracking location of the tag in the space, for example, as described in additional detail below.

Optionally, wearable monitoring device 1020 includes one or more activity sensors 1024 that sense one or more gestures of the subject within the space, such a limb gestures, and/or one or more postures of the subject within the space, for example, sitting, lying down, standing, running, crawling, and walking. Examples of activity sensors 1024 include: an accelerometer that measures linear acceleration, and a gyroscope that measures angular acceleration. The accelerometer and/or gyroscope improve resolution of gestures and/or postures, which may increase the accuracy of detecting the subject's actions. For example, data from the gyroscope may increase accuracy of the fall-detection, by enabling detecting of a broader set of body gestures that are associated with the dynamics of a real fall, and/or that are associated with a false fall.

Data from position tags 1022 and/or activity sensors 1024 may be analyzed to provide the body movement data described herein.

Alternatively or additionally, wearable monitoring device 1020 includes one or more physiological sensors 1026 that sense one or more physiological parameters of the subject within the space. The physiological parameters represent wellbeing of the subject. Optionally, the physiological sensor is a vital sign sensor that measures one or more vital sign parameters, for example, a heart rate sensor, a heart rate variability sensor, an oxygen saturation sensor, a respiratory rate sensor, and a skin temperature sensor. The physiological data in combination with the gesture data and/or postural change data and/or the subject location information may improve reliability of the contextual analysis for detection of the abnormal event, as described herein.

Wearable monitoring device 1020 communicates with a remote monitoring server (RMS) 1032, directly, and/or through one or more anchor devices 1028, and/or through an intermediary local monitoring unit (LMU) 1036. Optionally, remote monitoring server 1032 contains program instructions (as software and/or hardware components) that receive the tracked location of the subject within the space, the gesture data, the postural data, the body movement data, and/or physiological parameter data, analyze the tracked location to detect a location and/or body movement of the subject; and generate an alert indicative of an abnormal event(s) based on a contextual analysis of a correlation of a combination of the location and/or body movement data and the gesture(s) and/or posture and/or the physiological parameter(s). Optionally, local monitoring unit 1036 receives data representing the tracked location and/or body movement of the wearable monitoring device from the anchor devices, calculates the location and/or body movement of the wearable monitoring device, and transmits the calculated location and/or body movement to the remote monitoring server 1032 for further processing.

Local monitoring unit 1036 may be integrated with and/or incorporate the functionality of a base-station that works with a standard personal emergency response system (PERS), for example, local monitoring unit 1036 receives the indication of a button pressed on the mobile PERS.

Optionally, position tag 1022 is active, periodically (or continuously) transmitting distance indication message(s) for receipt and processing by anchor device(s) 1028. The distance indication messages are processed to determine the location and/or track the position of position tag 1022 relative to the anchor devices 1028, based on analysis methods, for example, based on receive signal strength (RSS), and/or time of arrival (TOA). Alternatively or additionally, the position tag is passive, receiving distance indication message(s) transmitted by the anchor device(s) 1028. The position tag may process the received message(s), to determine the location and/or track the position of the position tag relative to the anchor devices.

The position track functionality and/or transmission of other wireless communication messages between communication elements of the wearable device (e.g., voice communication) may be implemented using one or more air interface standards and/or protocols, for example, ZigBee®, WiFi®, Bluetooth®, and cellular network based protocols. The air interface may be dynamically selected (or pre-defined) based on location, for example, when indoors, the interface used by a voice communication module and the interface used by the positioning tag may be the same (e.g., to reduce costs). Alternatively, different interfaces are selected for different functions, for example, based on: intermediate concrete wall barriers, distance to anchor devices, and interference reduction.

Figure 2:
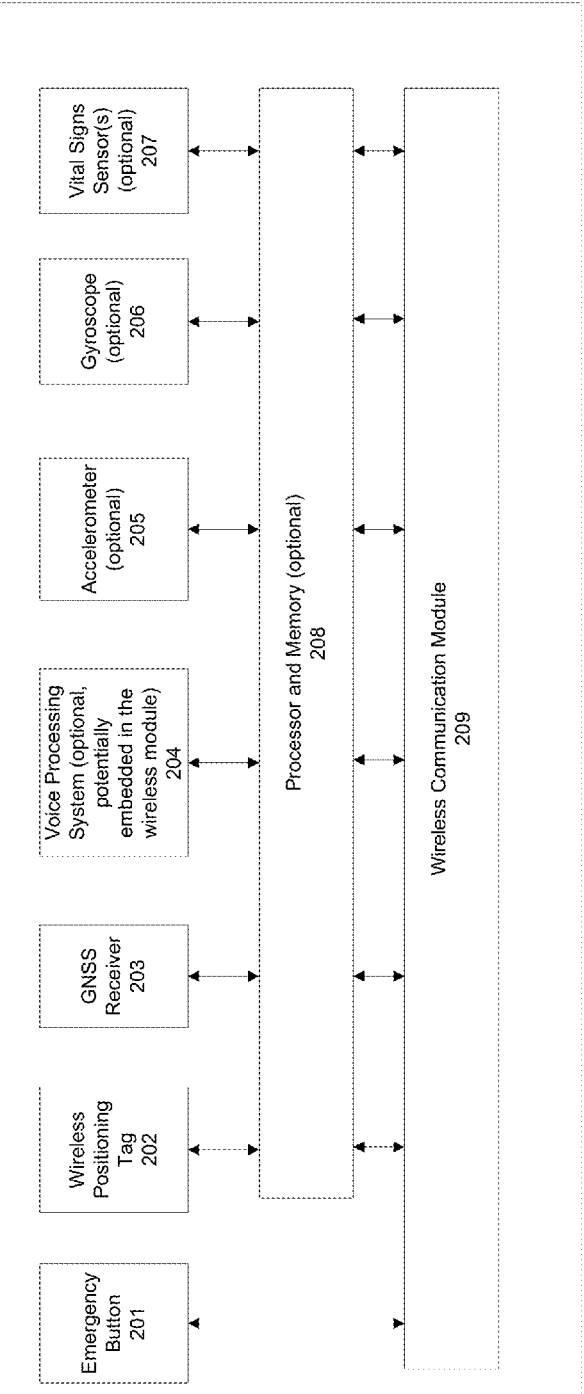
FIG. 2 is a block diagram of an example implementation of a wearable monitoring device, in accordance with some embodiments of the present invention.

Reference is now made to FIG. 2, which is a block diagram of an implementation of wearable monitoring device 200, such as wearable monitoring device 1020 of FIG. 1B, in accordance with some embodiments of the present invention.

Optionally, wearable monitoring device 200 includes an emergency and/or panic button 201, that when pressed by the subject, generates an alert to a caregiver, for example, to a family member, a physician, and a nurse providing remote monitoring. The alert may be locally processed by a local monitoring unit (e.g., unit 1036 of FIG. 1B), which sends an alert message to a respective remote location, for example, an email to a computer, a phone call to a phone, and a network message to a remote monitoring server.

Optionally, wearable monitoring device 200 includes a wireless positioning tag 202, as described herein. Alternatively or additionally, wearable monitoring device 200 includes a global positioning element 203, for example, a global positioning system (GPS) module, a global navigation satellite system (GNSS) receiver, and/or other space based navigation components. Global positioning element 203 generates location and/or body movement data of the subject. Element 203 may be used instead of tag 202, and/or when tag 202 is out of range of the anchor devices, for example, when the patient is outdoors, or at a different floor. The space based location may be transmitted for further processing via wireless communication module 209, as described herein.

Optionally, wearable monitoring device 200 includes a voice processing system 204. System 204 includes a microphone and a speaker for one or two-way voice communication with a remote caregiver and/or remote monitoring facility. System 204 may be embedded in a wireless module 209, allowing direct and/or indirect voice communication with the caregiver and/or remote monitoring facility.

Optionally, wearable monitoring device 200 includes one or more accelerometers 205 and/or one or more gyroscopes 206 as implementations of the activity sensor described herein. Sensors 205 and/or 206 may be based on microelectromechanical systems (MEMS) technology. Alternatively or additionally, wearable monitoring device 200 includes one or more vital sign sensors 207 as implementation of the physiological parameter sensors, as described herein.

Optionally, wearable monitoring device 200 includes a processor and a memory 208 in communication with the processor storing program instructions to execute one or more functions described herein. Alternatively or additionally, device (all or portions thereof) 200 is implemented in hardware.

Wearable monitoring device 200 includes wireless communication module 209 to communicate with the local monitoring unit, the remote monitoring server, another server, and/or anchor devices, using one or more air interfaces, as described herein. Communication module 209 (and/or components of device 200, for example, the position tag) may communicate directly with the local monitoring unit and/or directly with the remote monitoring server. Alternatively or additionally, communication module 209 indirectly communicates with the local monitoring unit and/or directly with the remote monitoring server via an intermediate computer, for example, a network connected mobile device (e.g., Smartphone, Tablet, Laptop) and/or a network connected desktop computer. It is noted that the mobile device and/or desktop may act at the local monitoring unit. The indirect communication may reduce cost and/or power consumption of the wearable monitoring device 200, by using the power and/or more powerful transmission capabilities of the mobile device.

Figure 4:
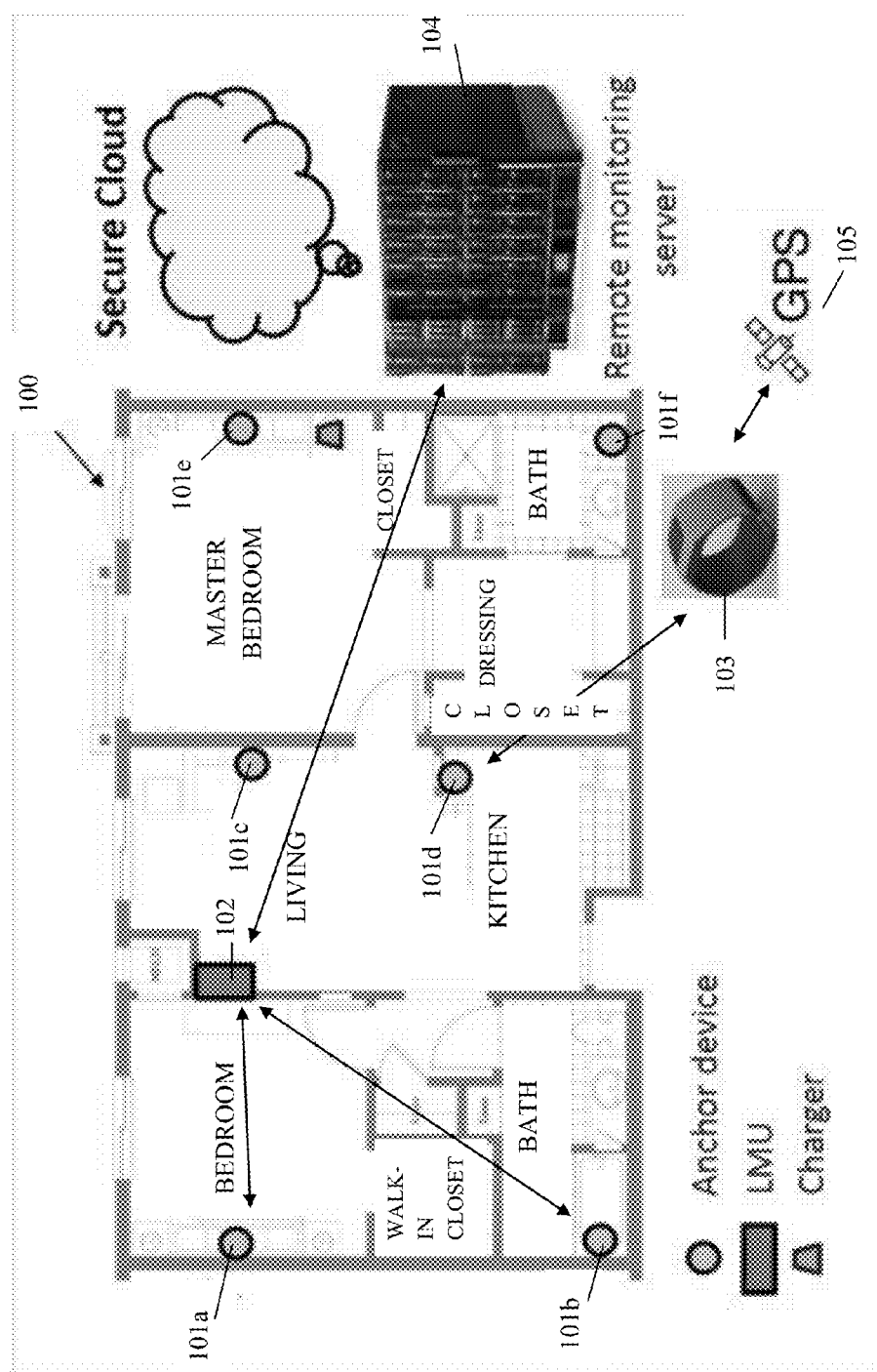
FIG. 4 is a schematic depicting an example of an environmental installation of the system for detection and monitoring of context based activities, in accordance with some embodiments of the present invention.

Reference is now made to FIG. 4, which is a schematic depicting an example of the system for detection and monitoring of contextually analyzed activities (e.g., system 1018 of FIG. 1B), in accordance with some embodiments of the present invention. The system may be deployed within a home environment 100 of the subject, represented by a floor plan. The subject is provided with a wearable monitoring device 103 implemented as a bracelet. Multiple anchor devices 101*a-f*, each containing one or more position sensors, are deployed within home 100, to provide coverage within the home of the subject. A local monitoring unit 102 deployed with home 100, communicates with anchor devices 101*a-f* and/or with monitoring device 103, as described herein. A remote monitoring server 104, which may be implemented within a secure computing cloud environment, communicates with multiple locally deployed LMUs 102. Remote monitoring server 104 may provide coverage for multiple home environments. Optionally, outside of the home environment, location and/or body movement is based on signals received by device 103 from a GPS satellite 105, as described herein. Optionally, device 103 contains a battery which is locally charged using a charger installed in the home environment.

Wearable monitoring device 103 may be designed for indoor only use, outdoor only use, and/or both indoors and outdoor use. For example, outdoor use devices may (as compared to indoor use devices) include a global positioning system (as described herein), have increased battery life, include a more powerful transceiver, be more resistant to falls, and made waterproof. The environment consideration may reduce cost, by including components where they are needed.

Figure 3:
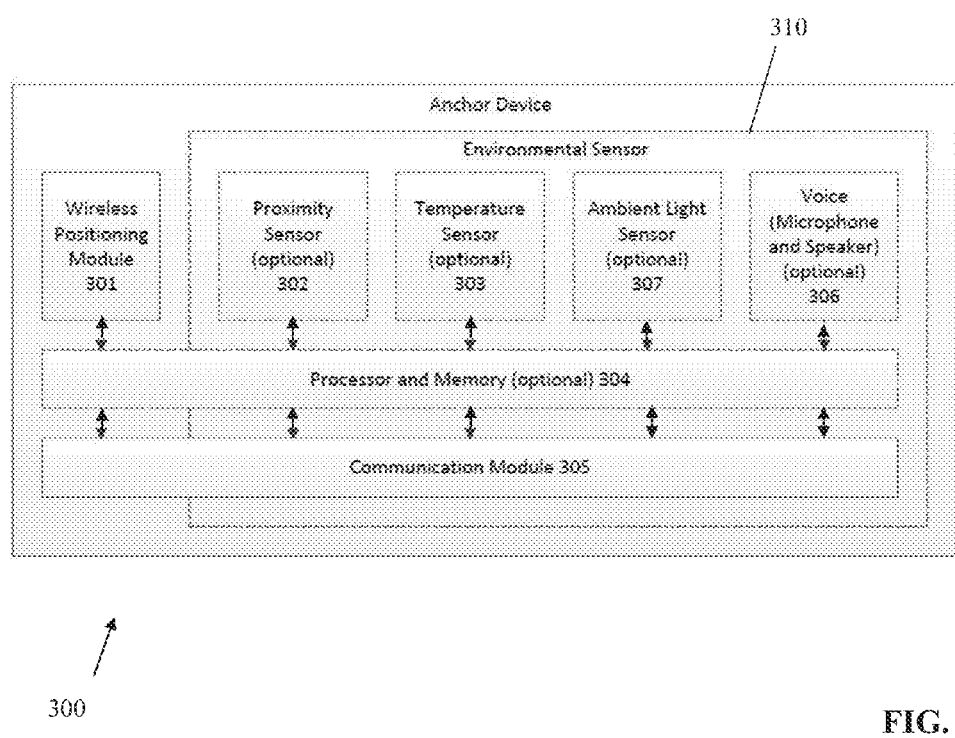
FIG. 3 is a block diagram of an example implementation of an anchor device, in accordance with some embodiments of the present invention.

Reference is now made to FIG. 3, which is a block diagram of an example implementation of an anchor device 300, such as anchor device 1028 of FIG. 1B, in accordance with some embodiments of the present invention. Anchor devices 300 are part of a positioning system, to detect the location of the wearable monitoring device (i.e., which detects the position of the subject wearing the monitoring device) within a space, such as a home environment. The positioning system may operate at different spatial resolution levels, for example, detection of the subject within certain rooms, detection of the subject within the room within about 1×1 meter, or about 0.5×0.5 meter, or other resolutions. The positioning system may have a resolution fine enough to detect the presence of the subject interacting with objects (e.g., fridge, bed, toilet, shower, wall, kitchen counter), for example, about 1 square meter, or about 0.5×0.5 meter, or about 0.3×0.3 meter, or other smaller, intermediate or larger resolutions. The positioning system may have a resolution fine enough to detect changes in height of the subject (e.g., standing, sitting, lying on a bed, lying on a floor), for example, about 1 meter, or about 0.5 meter, or about 0.3 meter, or other smaller, intermediate or larger resolutions. The wearable device is designed for integration with positioning systems, such as by being designed for communication with anchor devices of the positioning system. One example of a positioning system is described with reference to U.S. Provisional Application No. 61/908,767.

The locations of anchor devices 300 within the home environment may be pre-defined (e.g., obtained during installation), and/or obtained by the self-mapping scheme described with reference to U.S. Provisional Application No. 61/908,767. The self-mapping scheme may be performed, for example, by manually deploying the anchor devices in different locations in the space (e.g., home environment), and activating an automatic calculation of respective locations of each anchor device. The self-mapping is based on capturing by certain anchor devices, relative distance indication messages transmitted from other anchor devices. Distance indicative parameters indicative of respective distances between respective pairs of anchor devices are calculated based on the relative distance indication message. The distance indicative parameters are aggregated. A dataset which maps a location of each one of the anchor devices in the space according to the aggregated distance indicative parameters is calculated.

The LMU may communicate with the anchor devices, for example, through a control and data link (CDL), for example, as described in U.S. Provisional Application No. 61/908,767.

Optionally, when the wearable monitoring device includes an active position tag, anchor device(s) 300 receive the transmitted signal and measure reception parameters related to location tracking (e.g., RSS and/or ToA). The reception parameters are transmitted to the LMU and/or to the remote monitoring server from a wireless or wire-line communication module 305. The LMU and/or the remote server calculate the position of the position tag within the space based on the parameters received from multiple anchor devices. Alternatively or additionally, when the wearable monitoring device includes a passive position tag, anchor device(s) 300 transmit signal(s) that are received by the tag. The tag measures the reception parameters. These parameters may be transferred to the LMU and/or the remote server for calculation of position, and/or the tag may calculate its own position.

Alternatively or additionally, the location of the wearable monitoring device is calculated based on radiofrequency (RF) finger-printing scheme. The RF finger-printing scheme may be implemented based on the following computerized method: In a first phase RF signature(s) of a place (e.g., a bathroom, a bed in a bedroom) in the space (e.g., home premises) is captured as the finger-print set of received signal strength (RSS) received by multiple anchor devices receiving messages transmitted by the wearable monitoring device located in the place. Alternatively or additionally, the anchor devices transmit the messages and the wearable monitoring device measures the set of RSS received from each anchor device. In a second phase, sets of RSS received by the anchor devices (and/or by the wearable monitoring device) are compared to the finger-printing set to determine the estimated wearable monitoring device's location (e.g., by calculating the location in which some measure of RSS distance between the current RSS set and the finger-print set is minimal). The location may be determined at a resolution of the place (e.g., a room-level resolution, and an object level resolution). The RF finger-printing scheme may be implemented, for example, by an RF location module stored on, or in communication with, one or more anchor devices, the wearable monitoring device, the LMU, the RMU, and/or other computers.

A communication module 305 acts as a transceiver to facilitate communication with other anchor devices, the wearable monitoring device, the position tag, the local monitoring unit, the remote monitoring unit, and/or another mobile device.

A wireless positioning module 301 within anchor device 300 may receive the reception parameters from the wearable monitoring device.

Environmental sensing module 310 includes one or more sensors that sense one or more parameters of the close environment (e.g., within the room), as described herein, such as proximity sensor 302, temperature sensor 303, ambient light sensor 307, and voice system 306. Module 310 may include processor and memory 304, and communication module 305.

Module 310 may be a standalone device separate from anchor device 300, or integrated within anchor device 300.

Optionally, environmental sensing module 310 includes a proximity sensor 302 (e.g., passive infrared sensor, and/or ultrasonic sensor) to detect the presence and/or movement of the subject (e.g., change in location) and/or other objects. The data from the proximity sensor may be used to provide contextual data for the contextual analysis, for example, movement of objects in a room. The data from the proximity sensor may provide complementary location information and/or an initial rough location estimation data (e.g., at room level) to the LMU, for example, to improve detecting in which room the subject is in. For example, location sensors within the anchor device may be selectively turned off or at a low power (e.g., to save power and/or reduce noise interference). Tracking may be initially roughly performed by the proximity sensor to detect in which room the subject is located within. There may be one proximity sensor to monitor each room. Sensors in proximity to the subject (e.g., in the same room) may be selectively activated based on the data from the proximity sensor. In this manner, the initial rough location may be further refined based on additional collected data to improve reliability and/or accuracy of the location of the subject.

Optionally, environmental sensing module 310 includes other environmental sensors, such as a temperature sensor and/or an ambient light sensor 303 to detect the temperature and/or light level in the room. The data from the temperature and/or light sensor may be used to provide contextual data for the contextual analysis, for example, to determine whether the room is hot or cold and/or if the lights have been switched on in the room. Certain gestures and/or postures and/or body movements may be normal for one temperature and light ranges, but abnormal for a different temperature and light ranges.

The sensor(s) data may be transferred to the LMU for processing, such as to determine context.

Anchor device include a processor for processing signals and/or reception parameters. Optionally, a memory 304 in communication with processor stores software components.

Alternatively or additionally, one or more program instructions are implemented as hardware.

Optionally, environmental sensing module 310 includes an audio sensor (e.g., microphone) and/or speakers 306 to provide audio communication between the subject and a remote caregiver, such as during identification of the abnormal event, as described herein.

At 1004, body movement and/or location data of the subject within the space is collected based on the wearable monitoring device. Gesture data and/or posture data and/or physiological data is optionally collected based on the wearable monitoring device.

The LMU and/or remote monitoring server may incorporate a central location unit that computes and/or tracks location of the wearable monitoring device (i.e., the location of the tag), based on received distance indicative parameters. The LMU and/or remote monitoring server may receive (directly or indirectly) posture and/or gesture and/or physiological parameters from the wearable monitoring device. Raw or processed information may be received from respective sensors of the wearable device. Raw or processed information may be received from sensors of the anchor devices, for example, the proximity and/or environmental sensors.

In some embodiments, the location and/or trajectory information used for the activity analysis is received from devices other that the positioning tag, for example, a three dimensional camera.

Figure 6:
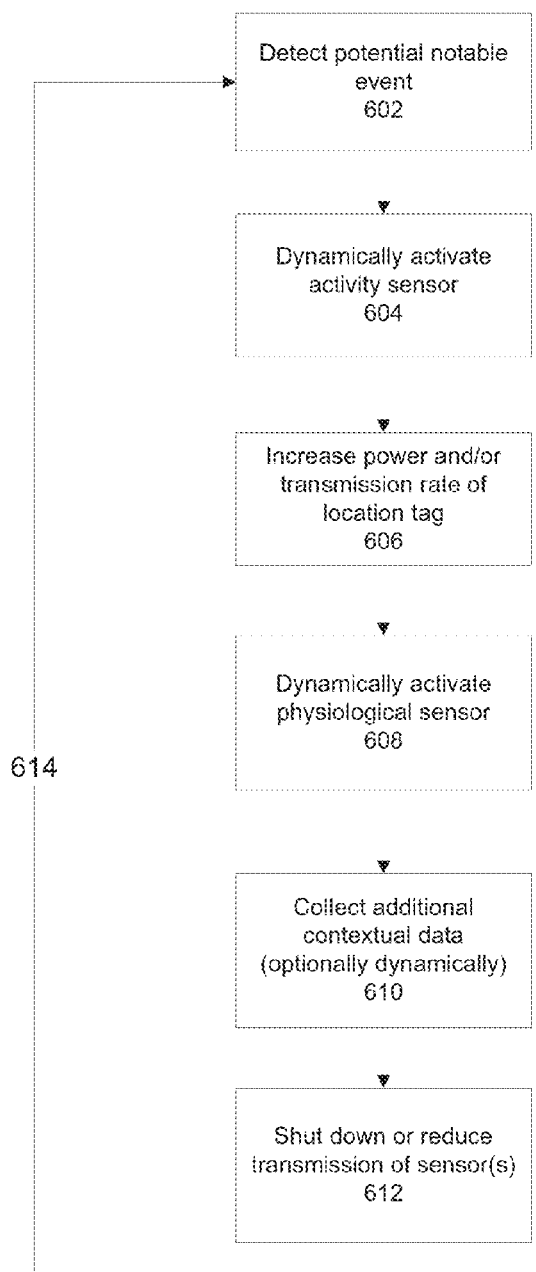
FIG. 6 is a flowchart of computer implemented method for dynamic activation of sensors, in accordance with some embodiments of the present invention.

Reference is now made to FIG. 6, which is a flowchart of computer implemented method for dynamic activation of sensors, in accordance with some embodiments of the present invention. The dynamic sensor activation method may be applied as energy saving measures to conserve the battery life of the wearable monitoring device. The dynamic sensor activation method may be applied to reduce noise interference, by activating sensors when needed. The dynamic sensor activation method may be provided to subjects and/or caregivers conserved with excessive exposure to electromagnetic radiation.

The dynamic activation of sensor method may be implemented by a software and/or hardware module residing within the wearable monitoring device, anchor device, LMU, RMS, or other computer. Sensors may be remotely activated by the RMS, the LMU, and/or one or more of the anchor devices. Sensors may be locally activated by the wearable monitoring device. Sensor activation may occur before the correlation and/or analysis, to provide additional data for the correlation and/or analysis, and/or after identification of the abnormal event, to confirm or retract the abnormal event based on the additional data.

At 602, a potential notable event is detected. Optionally, the subject is identified to be in a potential distress situation, and/or the subject is identified as being located in proximity to one or more predefined objects in the space, and/or when the subject is identified as performing a significant gesture.

At 604, activation of one or more of the activity sensors of the wearable device is dynamically performed. The sensors are dynamically activated when triggered based on the detected event. For example, the activity sensors are activated when the subject is detected as approaching the refrigerator. The activity sensors may be dynamically activated to measure body movement data. The activity sensors may be dynamically activated to measure gesture data and/or posture data in proximity of the refrigerator, for example, to provide additional correlation data.

Alternatively or additionally, at 606, wearable monitoring device is dynamically controlled to increase the rate at which messages are transmitted and/or power of transmission. The dynamic control of the wearable monitoring device may be performed based on the detected event and/or data collected by the activity sensor, such as to determine the position of the subject with increased accuracy when a significant gesture is detected.

Alternatively or additionally, at 608, physiological sensors are dynamically activated. Optionally, the physiological sensors are dynamically activated after the abnormal event is identified, to confirm the abnormal event when physiological parameters are abnormal, for example, a sudden increase in respiratory rate when delirium related body movements are detected. Optionally, when a patient distress event (e.g., fall, confusion, dizziness, delirium) is contextually detected based on location and/or body movement data, the heart-rate monitor may be activated. Detection of a very slow heart-rate, which may occur due to a post-fall faint, increases the reliability of the fall detection event.

Alternatively or additionally, the physiological parameters may be programmed for periodic dynamic activation, for example, the heart rate sensor is activated once every 30 minutes for a period of 30 seconds. The periodic activation may periodically monitor the subject, instead of, for example, continuously monitoring the subject. The periodic activation reduces power consumption of the wearable monitoring device. Alternatively or additionally, the physiological sensor is triggered to provide additional data, such as during certain gestures and/or certain subject locations which may be associated with abnormal events. For example, when (or soon after) the patient is identified as moving back and forth in the living room, the heart rate sensor may be activated to determine whether the patient is experiencing cardiac problems, is in stress, or is normally dancing (based on heart rate, and/or heart-rate variability analysis).

Alternatively or additionally, at 610, additional contextual data, such as environmental data, is collected. The additional contextual data may be dynamically collected and/or environmental sensors may be dynamically activated. Alternatively, the additional contextual data may be periodically and/or continuously collected.

The additional contextual data may be collected, for example, from external servers (e.g., date and/or time servers), from the environmental module described herein, from other sensors (e.g., the proximity sensors as described herein identifying other people in the room beside the subject), and from manual entry (e.g., subject pressing a button after taking medications).

Optionally, at 612, the power of one or more sensors is reduced, to shut down or reduce transmission rate and/or power of the sensors. The power reduction may be dynamically triggered after the normal or abnormal event has been detected.

Optionally, at 614, one or more blocks 602-612 are iterated, to dynamically adjust the sensor power, as described herein.

Referring now back to FIG. 1A, at 1006, the body movement data is correlated with the subject location data. Alternatively or additionally, the gesture(s), postural changes, and/or the physiological parameter(s) are correlated with the body movement and/or location data. The correlation may be performed locally by the LMU, and/or remotely by the remote monitoring server. The correlation may be performed in view of one or more contextual data items, for example, based on time, based on location of the subject, based on identified sequence of events, and/or other suitable methods.

Optionally, the body movement and/or location data is correlated with the gesture data and/or the posture data. Alternatively, the body movement and/or location data is correlated with the gesture data and/or the posture data and the physiological parameters. Alternatively, the body movement and/or location data is correlated with the physiological parameters.

The correlation may improve accuracy of detection of the abnormal event. For example, when the subject's location is identified as being next to a refrigerator, gestures and/or posture data is captured of the subject raising a hand to grab the door handle, then pulling back the hand to open the door. The gesture and/or postural changes correlated with the body movement and/or location data helps distinguish, for example, between a case where the subject is standing with his/her back to the refrigerator and performing random motion in the air with his/her hands (i.e., abnormal event), and the case when the subject is opening the refrigerator door in a normal fashion (i.e., normal event). The subject may be tracked approaching the kitchen table and sitting to eat the meal obtained from the fridge. The analyzed posture data may represent postural changes, such as the subject moving from a standing posture to a sitting posture. The postural change, when combined with body movement and/or location data (i.e., the subject's current location next to the kitchen table, and optionally the trajectory from the refrigerator to the kitchen table) increases the accuracy of detecting that the subject is eating a meal in the normal fashion, instead of, for example, sitting down due to chest pain. The postural change in combination with body movement and/or location data may be identified as normal activity, by having a correlation that is similar to previous combinations of similar postural changes in similar context known to be normal meal eating activities. Details of analyzing the correlation are described, for example, with reference to block 1008.

The combination of the body movement and/or location data and physiological information may improve the assessment of the subject's wellbeing, when the abnormal event is defined as a reduced wellbeing without a specific cause that is identifiable by the system. For example, when the heart-rate of the subject is measured as statistically significantly higher or lower than the normal value with a similar context, and a deviation in gesture is identified (e.g., the subject doesn't follow a similar morning routing of visiting the bathroom, the kitchen and then the living room), an abnormal event is identified. In another example, identification of abnormal heart-rate variability (HRV) (i.e., abnormal HRV is a symptom of stress), within a similar body movement and/or location data is associated with an abnormal event. The similar body movement and/or location data acts as a flag that the abnormal heart patterns that the user is experiencing are caused by an underlying medical event significant enough to prevent following normal routine.

At 1008, the correlation is contextually analyzed to identify one or more abnormal events. Alternatively or additionally, the correlation is contextually analyzed to identify one or more normal and/or expected events. The analysis may be performed locally by the LMU, and/or remotely by the remote monitoring server.

The contextual analysis may be performed based on comparison of the location trajectory of the subject relative to the objects in the space, to trajectories of other subjects relative to other similar objects in each respective space of the different subjects. For example, comparison to trajectories of other subjects in the vicinity of their respective refrigerators and kitchen tables may detect and/or improve the accuracy of detecting the meal preparation and/or eating activity.

The contextual analysis may be performed, for example, by a machine learning module applied to a training dataset, for example, a statistical classifier. The contextual analysis may be performed, for example, by an automated learning module, based on supervised learning or unsupervised learning methods.

Predetermined locations of objects within the space are determined, for example, based on a tagging of each respective object during an installation process, based on a predefined floor plan of the space of the subject that includes locations of the objects relative to the floor plan, and/or based on a self-constructed floor plan, for example, as described with reference to U.S. Provisional Application No. 61/908,767.

Information on the location of portions of the environment may be available (e.g., identifying the subject in the kitchen, or in the living room). Partial or no information may be available on the location of key objects in the respective portion (for example, the location of the refrigerator in the kitchen is available, but the location of the kitchen table is not available. In another example, no object within the kitchen is available). In such a case, the position and/or body movement data and/or gesture and/or posture information is analyzed to deduce the location of the key objects. For example, when the position of the refrigerator is known, the location of the kitchen table may be deduced based on tracking the trajectory of the subject from the fridge, and/or the location in the kitchen at which the change from standing to sitting posture occurs.

Alternatively or additionally, the location of the refrigerator is detected (i.e. when not known apriority) by comparing the combination of position, trajectory, gesture and/or posture information of the subject, to information stored in a data-base of similar combinations of other subjects when they approach to open the refrigerator. When a similar combination occurs (and repeats itself several times in the same location), the system automatically learns the location of the object.

Optionally, the correlation is contextually analyzed to identify one or more activities of the subject. The correlation is contextually analyzed based on activity related location and/or location trajectories of the subject (e.g., calculated based on the tracked location). The location trajectories are contextually analyzed relative to locations of one or more objects within the space of the subject, which may be predetermined absolute locations, dynamic locations (e.g., chairs moved around), and/or relative locations (e.g., sofa is next to a coffee table). Each object is associated with one or more activities, which provide context data. For example, when the subject is identified as lying on the bed longer than a predefined period of time (e.g., 15 minutes), the activity may be identified as sleeping. In another example, when the subject is identified as walking between the fridge and the kitchen table, the activity may be identified as eating and/or preparing a meal. Each activity may be analyzed to determine whether the activity represents a normal activity, or an abnormal event.

Optionally, the analysis is identified based on a sequence of related gestures and/or postures, such as correlation between gestures and/or postures in a sequence. For example, the activity of preparing and eating a meal includes gestures, postures and/or subject body movement such as opening the refrigerator door, moving from the refrigerator to the kitchen table, sitting next to the table, and the eating.

Each portion of the sequence may be analyzed independently to detect one or more abnormal events for each portion of the sequence, for example, based on extracted parameters of the detected activity, such as duration of the activity (e.g., duration of preparing and eating the meal), and/or duration of sub-phases of the activity (e.g., duration of eating only). For example, detecting the subject sitting down on the floor to eat the meal (i.e., abnormal) instead of at the table (i.e., normal). Alternatively or additionally, the sequence may be analyzed in its entirety to detect the abnormal event. For example, detecting that the subject missed lunch entirely.

Alternatively or additionally, the contextual analysis is based on the physiological parameters. For example, the heart rate of the subject may be sampled periodically (e.g., every 30 min) to assess normal heart-rate range of the subject. A heart rate that is significantly lower than the lower range, or significantly higher than the higher range may represent a potential abnormal event. The heart rate information is correlated with the body movement and/or location data. For example, when the body movement and/or location represents the subject being located in the bathroom and not moving for a period of about 10 minutes, is correlated with a drop in heart-rate below the lower threshold (e.g., 40 beats/minute), the abnormal event is detected. The low heart-rate (i.e., physiological parameter) may detect the abnormal event faster (e.g., without the heart-rate information, an additional 20 minutes of non-movement in the bathroom may be required to reliably detect the abnormal event). Alternatively, the body movement and/or location may distinguish between the case in which the low heart rate is normal for the subject (e.g., electrical and/or medication based rate control), but the non-movement in the bathroom for over 10 minutes is abnormal.

In some embodiments, the LMU executes a preliminary analysis to identify significant abnormal events based on the subject's behavior. For example, a deviation from past recorded routines of the subject, based on comparison to a limited set of past recorded data (e.g., stored locally at the LMU). When a potential abnormal event is detected, the LMU may transmit the result and/or data to the RMS for confirmation. When no abnormal event is detected, the LMU may transmit the result and/or data to the RMS for additional analysis. The RMS may execute an advanced analysis to detect deviation from recorded routines of other subjects and/or more data of the same subject, for example, based on comparison to a broad set of past data (e.g., stored at the RMS) of the same subject, and/or based on aggregated past information from other subjects.

Alternatively, in another implementation, the analysis is performed locally at the LMU. Alternatively, in another implementation, the analysis is performed remotely at the RMS.

Optionally, the correlation is contextually analyzed to identify one or more activities of daily living (ADLs), for example, by an activity monitoring and/or analysis module stored on or in communication with the LMU and/or the remote monitoring server. The activity of daily living may be analyzed to identify the abnormal event related to the identified activity of daily living. Examples of activities of daily living include: eating, sleeping, bathing, dressing, grooming, watching television, and vacuuming the carpet. Activities of daily living may be considered as normal, such as when performed within an expected context, at an expected time of day, and/or in an expected manner. Activities of daily living may be considered as abnormal events, when deviating from the normal expected activity of daily living, such as missing an activity, performing too many of the same activity, performing the activity in an abnormal manner, and performing the activity at an unexpected time of day.

The contextual analyzing of the correlation may be performed to identify the abnormal or normal event based on comparison of a current trajectory of the subject to past trajectories of the same subject representing normal or abnormal events, and/or trajectories of other subjects representing normal or abnormal events. The current trajectory is compared to similar trajectories (e.g., within a margin of tolerance), for example, within a similar location, such as within the same bedroom, and/or within different locations having a similar context, for example, different rooms each having a sofa, a television and a coffee table. Trajectories may be compared when the resolution of the subject position is at a room level, for example, the pattern of changes in location of the subject from room to room, for example, in the morning the subject location in the bedroom, then in the bathroom, then the kitchen, and then in the dining room (representing a normal morning routine trajectory).

The contextual analysis of the correlation may be performed based on a learned routine data set stored within an activity database. The activity database may store one or more normal and/or abnormal routines of the subject, to identify an abnormal event (i.e., not included in the normal database and/or included in the abnormal dataset) or to identify a normal event (i.e., included in the normal database and/or not included in the abnormal dataset). The activity database may store learned data representing combinations of tracked subject location data correlated with subject gesture and/or posture data representing different activities and/or physiological data representing different activities. Each combination may be associated with a normal or abnormal routine of the subject. Alternatively or additionally, the learned routine data set includes multiple normal and/or abnormal routines learned from multiple different subjects.

The learning may be performed based on, for example, manual tagging, predefined tags, outcomes of previous automatic identification of abnormal (or normal) events, supervised learning, and/or unsupervised learning. A machine learning module may apply the received data to the stored data set to identify the abnormal activity, for example, a statistical classifier. A probability or an absolute result of the abnormal activity (or normal activity) may be provided as an outcome.

The data within the activity database may be collected based on one or more of: past data of the same subject, data from other similar subjects, and/or data from other similar subjects having similar medical conditions as the subject. For example, data within the activity database may be collected from patients suffering from restless movement disorder. Repetitive gestures of similar location trajectories within a certain context during a predefined period of time of the subject (e.g., worsening when at rest on a sofa or a bed, and improving during motion such as walking) may be analyzed based on the restless movement disorder dataset to identify a possible restless movement disorder event.

Optionally, activity database 1034 is stored on, or in communication with remote monitoring server 1032. Alternatively or additionally, the activity database (in whole, in part, or a copy thereof) is stored on, or in communication with local monitoring unit 1036. Remote monitoring server 1032 and/or local monitoring unit 1036 use activity database 1034 to identify the abnormal event, as described herein.

It is noted that when the emergency button is pressed on the wearable monitoring device (e.g., by the subject, or by a passerby), the abnormal event is automatically identified, overriding any performed analysis of the context, gesture, posture, and/or physiological parameter data (i.e., the analysis may not necessarily be performed in such a case).

At 1010, an alert indicative of the abnormal and/or normal event is generated, for example, by remote monitoring server 1032 and/or local monitoring server 1036. The alert message may be automatically transmitted to an external entity, such as the caregiver, as described herein. Optionally, an audio monitor for communication between the subject and the caregiver is automatically activated upon generation of the alert, allowing the caregiver to listen to the subject.

Optionally, the alert is generated when the abnormal event represents one or more of: a deviation from the normal routine, a distress situation, and a deviation from an activity trend. Alternatively or additionally, the alert is generated when the abnormal event represents one or more of: a fall, a crawl, abnormal gait, and restless movement disorder. Alternatively or additionally, the alert is generated when the probability of the abnormal event is identified above a certain threshold.

Optionally, the audio monitor (e.g., included within the wearable monitoring device and/or the anchor device), is triggered when the abnormal event is detected. When the audio sub-system is included in the anchor devices, the audio system of the anchor device closest to the location of the subject is triggered (e.g., using the tracked location of the subject). A recording of the subject and/or 2 way audio communication may be established with the caregiver.

An example use case detects a distress event of the subject, based on the systems and/or methods described herein. The distress event may be based on one or more underlying conditions, for example, a fall, delirium, confusion, disorientation, and dizziness. The systems and/or methods described herein increase the reliability of detection of the distress event based on contextual analysis, identifying distress event in context within the home environment (or other spaces) where distress event are more likely to occur. Optionally, machine learning occurs dynamically based on an analysis of the trajectories of the subject in the home environment, including locations in which the subject is expected to be stationary, location in which the subject is expected to be moving, and a normal rate of movement in each respective location.

A fall is detected based on identifying a location of the subject. For example, identifying that the subject is static for a predefined period of time in a location where the subject usually walks. Optionally, normal routine information and/or time of day information are added to further increase the reliability of detection of the fall event. For example, the subject being stationary in the corridor for a period of 10 minutes at 3 AM.

Optionally, a fall gesture data and/or postural data, such as a sudden change in position from standing to lying on the floor, may be added to further increase the reliability of detection of the fall event.

The location of the fall and/or body movement trajectory leading to the fall may be analyzed relative to predefined objects within the home environment, to determine whether or not a fall event has occurred. The fall event is detected when the fall gesture and/or postural change occurs in a location where a fall is more likely to occur (e.g., stairs, entrance to building, middle of the room), and the fall event is not detected when the fall gesture occurs in a location where a fall is less likely to occur (e.g., on a bed, on a sofa).

For example, the fall event is identified when the subject is found to be stationary in a place where the subject normally moves for a period of time that exceeds a predefined threshold (e.g., house corridor, or street). In another example, the fall event is identified when the subject moves at a rate that is significantly below the normal rate for the respective location (e.g., slowly crawling in a corridor and/or on the street, instead of normally walking faster).

In another example use case, abnormal gait patterns are detected based on the contextual analysis. Gait information is collected based on gesture and/or posture (e.g., accelerometer data) and/or information on the subject's trajectories. The gesture and/or trajectory information includes absolute and/or relative body movement information (e.g., absolute step size, or relative change in step size). When the advanced gait analysis is correlated with the subject's location in the environment (as described herein), the gait and/or changes in the gait are analyzed with respect to certain locations, for example, in the living room. The contextual analysis differentiates between relatively open spaces in the house and constrained environments in the house (e.g., the shower, the bathroom). The contextual analysis approach is based on determining influences of different environments on the gait of the subject. For example, an abnormal gait event is detected based on identification of a decrease in step size when the subject walks in the living room compared to the step size in the same location a month ago. The contextual analysis prevents masking of the step size change by a decrease in the step size limited by the environment, for example, when the subject walks in the shower room (e.g., simple time averaging may mask the effect of the step size reduction).

Figure 5:
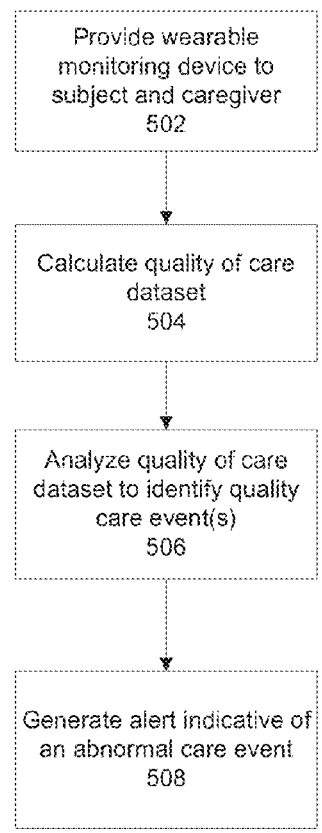
FIG. 5 is a computer implemented method for monitoring quality of care provided by a caregiver to a subject, in accordance with some embodiments of the present invention.

Reference is now made to FIG. 5, which is a computer implemented method for monitoring quality of care provided by a caregiver to a subject, and generating an alert upon detection of an abnormal care event, in accordance with some embodiments of the present invention. The method calculates a quality of care dataset, which is analyzed to provide an indication of the quality of the care provided by the caregiver to the subject. The quality of care dataset may be monitored to identify the abnormal care event and/or provide a representation of quality of care over a predefined period of time. The method may be executed, for example, by system 1018 described with reference to FIG. 1B.

At 502, a wearable monitoring device including one or more position tags is provided to a caregiver, and another wearable monitoring device including one or more position tags is provided to a subject being cared to by the caregiver. The caregiver provides care directly to the subject, for example, a full time attending nurse providing care to a patient with chronic disease, a child taking care of an elderly parent, and a hired worker to help an elderly person live at home. The wearable monitoring device and position tags are, for example, as described herein. The relative position may be tracked, for example, by anchor devices as described herein.

At 504, a quality of care dataset is calculated. The quality of care dataset may include one or more quality of care metrics that represent a measure of interaction between the subject and the caregiver, which may be correlated with quality of care. The quality of care metrics may be selected based on the subject, for example, care for elderly patients with Alzheimer's may be monitored differently than care for an independent person with cardiac disease.

Optionally, the quality of care dataset includes data based on the relative tracked locations of the position tag of the subject relative to the position tag of the caregiver. Quality of care metrics may be calculated from the dataset based on one or more of:

An average of a distance between the caregiver and the subject as a function of time. An average close distance may represent high quality care, for example, suggesting that the caregiver being close to the subject provides better attention to the needs of the subject. An average far distance may represent low quality care, for example, suggesting that the caregiver being far from the subject provides insufficient care to the needs of the subject.

A maximal of the distance. One or more events in which the caregiver is far from the subject may indicate low quality of care, for example, suggesting that the caregiver is leaving to attend to personal errands (e.g., going to the bank) while the subject is left alone. A low maximal distance may suggest high quality of care, for example, suggesting that the caregiver is always close by to offer help.

A function of the distance over time. The amount of time spent close to the subject may indicate quality of the care. For example, when the caregiver spends long periods of time close to the subject, the subject may be receiving high quality care. When the caregiver spends long periods of time away from the subject, the subject may be neglected suggesting low quality of care.

Alternatively or additionally, the quality of care dataset is calculated based on an identified sequence of gestures, locations, and/or postures of the caregiver and/or the subject. The sequence of gestures and/or postural changes may be compared to learned sequences (e.g., by a statistical classifier) to detect degrees of deviation from the reference pattern. The quality of care metric may be based on the probability of matching a predefined correct sequence or a predefined improper sequence.

The gestures and/or postures may be measured by activity sensor(s) installed within respective wearable monitoring devices of the subject and/or caregiver, for example, as described herein. Certain gestures and/or postures may be associated with high quality or low quality (or other quality levels) of care. For example, gestures and/or postures associated with the caregiver feeding and/or washing the subject may indicate high quality care. Gestures and/or postures associated with the caregiver performing other personal tasks may indicate low quality care. The sequence of gestures and/or postures may be analyzed based on machine learning (e.g., statistical classifier) including training data gathered from the same caregiver and/or different caregivers performing pre-defined good care or bad care on the same subject and/or different subjects. The caregiver may be taught the sequence of events, which are recorded by the system and incorporated into a training dataset (e.g., for training a classifier or other machine learning system). For example, the caregiver is supervised and directed to perform a sequence of actions to the subject as part of a routine to be repeated on a regular basis.

Alternatively or additionally, the quality of care dataset is calculated based on an analysis of voice data generated by the subject calling the caregiver. The voice data may be gathered and/or analyzed based on a voice system within the wearable device, the anchor devices, within other units, and/or a standalone system, for example, as described herein. Metrics are calculated based on the responsiveness of the caregiver to the calling subject, measured based on changes in the relative locations of the position tag of the subject relative to the position tag of the caregiver that occur after the subject has called the caregiver.

The name of the caregiver (and/or other calls for help by the subject) may be manually programmed into the system, and/or automatically learned by analyzing voice data of the subject and the responsiveness of the caregiver. For example, by detecting repeated decreased distances between the caregiver and the subject, in response to the subject calling the caregiver by name (and/or other calls for assistance). Quality of care metrics based on the responsiveness of the caregiver may be calculated when the system identifies the subject calling the name of the caregiver. The quality of care metrics may provide an improved measure of when the caregiver responds to the subject calling for assistance.

The quality of care metric based on dataset of the responsiveness of the caregiver may be calculated based on one or more of:

Average response time, such as from the time the subject calls the caregiver until the caregiver arrives in near proximity to the subject. The average response time may be adjusted based on the measured distance, for example, response time per unit of distance. Fast response time may represent high quality care. Slow response time may represent low quality care.

Maximal response time. May detect when the caregiver decides to ignore the subject, or is otherwise unavailable for long periods of time. High maximal response time may represent high quality care. Low maximal response time may represent low quality care.

Predefined deviation from average response time, for example, within one or two standard deviations from the average. High variations in response time may represent low quality care. Low variations in response time may represent high quality care.

Response time in relation to a time of day. For example, response time during the night may be expected to be longer than during the day. A response time of 10 minutes during the day may represent low quality care, while the same response time of 10 minutes during the night may represent high quality care.

The quality of care data may be generated and/or quality of care metrics may be calculated, for example, by the local monitoring unit, by the remote monitoring unit, and/or by other external servers and/or local servers.

At 506, the quality of care metric dataset is analyzed to identify one or more abnormal events in care provided to the subject by the caregiver. One or more quality of care metrics may be calculated and analyzed. The quality of care dataset may be analyzed for discrete abnormal events occurring at certain points in time, for example, subject abuse by the caregiver, and the subject calling but not being responded to by the caregiver. The quality of care dataset may be analyzed for an overall picture of quality of care over a predefined period of time, for example, a work shift, a week, and a month. For example, to determine when the caregiver spends significant amounts of time close to the subject, or tends to ignore the subject.

Optionally, the quality of care dataset is analyzed based on a location and/or body movement of the subject and/or the caregiver. The location may be based on the location tracked by respective position tags, for example, as described herein. For example, detection of the caregiver spending time in the kitchen (i.e., food preparation context) may represent high quality care. In another example, when the caregiver and the subject are both detect as being in the bathroom at the same time for a period of time above a threshold, the quality of care metric may represent high quality in providing bathroom help.

Alternatively or additionally, the quality of care dataset is analyzed based on physiological data collected by physiological sensors within the wearable monitoring device, as described herein.

The gesture and/or postures and/or physiological data and/or location data may be correlated with one another (e.g., as described herein) when performing the quality of care dataset analysis. For example, a certain quality of care value may represent high quality of care within a certain combination of gesture and/or postures and/or physiological data and/or location, with the same value representing low quality of care within a different combination. For example, detection of the caregiver approaching the patient many times may at first suggest high quality of care. However, when physiological data is correlated with the dataset, the same value may suggest low quality of care or abuse. Such as when the subject's heart rate rises every time the caregiver approaches the subject. The increased heart rate may suggest a negative interaction for the subject by the caregiver, or abuse.

At 508, an alert indicative of the one abnormal care event is generated, for example, as described herein. The alert may be transmitted to a trusted source for further action, for example, a family member, the family physician, and the operating company sending the caregiver.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant systems and methods will be developed and the scope of the terms wearable monitoring device, position tag, activity sensor, physiological sensor, anchor device, and server are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computerized method of detection and monitoring of at least one position based activity by a subject, comprising:
   providing a wearable monitoring device including at least one position tag configured to communicate with a plurality of anchor devices, each device including at least one sensor configured for tracking location of the position tag in a space, the wearable monitoring device further configured to be detachable and wearable on a subject;
   collecting body movement and location data of the subject within the space based on the tracked location of the at least one position tag;
   providing at least one activity sensor configured to sense at least one body movement of the subject within the space, wherein the wearable monitoring device includes the at least one activity sensor;
   collecting body movement data based on the at least one activity sensor;
   correlating the body movement data and the location data and a time of day and day of week;
   contextually analyzing the correlation to identify at least one abnormal event or at least one normal event based on a deviation of the correlated subject body movement and the location data and the time of day and day of week from past recorded data of a previous combination of similar body movement data and location data and time of day and day of week; and
   generating an alert indicative of the at least one abnormal event or the at least one normal event;
   wherein contextually analyzing comprises contextually analyzing the correlation based on a learned routine data set storing at least one normal routine of the subject to identify the at least one abnormal event, and generating the learned routine data set based on learning at least one normal routine of the subject based on a pattern of the tracked location and at least one of: body movement, posture, gesture, and physiological parameters, recorded with the time of day, and day of week;
   wherein the learned routine data set includes at least one normal routine learned from a plurality of different subjects each similar to the subject.

2. The method of claim 1, further comprising:
   collecting postural data based on the at least one activity sensor;
   wherein correlating comprises correlating the postural data and the body movement and location data and the time of day and day of week; and
   wherein contextually analyzing comprises contextually analyzing the correlation to identify at least one abnormal event or at least one normal event based on subject body movement and location where the postural data is performed.

3. The method of claim 1, further comprising:
   collecting gesture data based on the at least one activity sensor;
   wherein correlating comprises correlating the gesture data and the body movement and location data and the time of day and day of week; and
   wherein contextually analyzing comprises contextually analyzing the correlation to identify at least one abnormal event or at least one normal event based on subject body movement and location where the gesture data is performed.

4. The method of claim 1, further comprising:
   providing at least one physiological sensor configured to sense at least one physiological parameter of the subject within the space, wherein the wearable monitoring device includes the at least one physiological sensor;
   collecting the at least one physiological parameter based on the at least one physiological sensor; and
   wherein correlating comprises at least one of correlating the at least one physiological parameter and the body movement and location data and time of day and day of week;
   wherein contextually analyzing comprises contextually analyzing the correlation to identify at least one abnormal event or at least one normal event based on subject body movement and location where the at least one physiological parameter is measured.

5. The method of claim 1, wherein contextually analyzing comprises contextually analyzing the correlation to identify at least one activity of daily living, and analyzing the at least one activity of daily living to identify the at least one abnormal event related to the at least one activity of daily living.

6. The method of claim 1, further comprising activating an audio monitor closest to the location of the subject according to a tracked location of the subject, for communication between the subject and a caregiver based on the identification of the at least one abnormal event.

7. A system for detection and monitoring of at least one position based activity by a subject, comprising:
   a wearable monitoring device configured to be detachable and wearable on a subject, comprising:
      at least one position tag configured to communicate with a plurality of anchor devices, each device including at least one sensor configured for tracking location of the at least one position tag in a space; and
      at least one activity sensor configured to sense at least one body movement of the subject within the space; and
   a monitoring unit configured to:
      receive body movement and location data of the subject within the space, and a time of day, and day of week;
      generate, based on a contextual analysis of a deviation of a correlation of the body movement and the location data and time of day and day of week from past recorded data of a previous combination of similar body movement data and location data and time of day and day of week, a message indicative of at least one abnormal event or at least one normal event; and
   an activity database storing learned data representing combinations of tracked subject location data and subject body movement data and/or gesture data and/or physiological data, correlated with time of day and day of week, representing different activities, wherein the activity database is in communication with the monitoring unit, and the monitoring unit uses the activity database to identify the at least one abnormal event, wherein the data within the activity database is collected based on one or more members of the group consisting of: past data of the same subject, data from other similar subjects, data from other similar subjects having similar medical conditions as the subject;

wherein:

the wearable monitoring device further includes at least one physiological sensor configured to sense at least one physiological parameter of the subject within the space; and the monitoring unit is further configured to receive the at least one physiological parameter; and generate faster than without the at least one physiological parameter, based on a contextual analysis of a correlation of the body movement and location data with the at least one physiological parameter, a message indicative of at least one abnormal event or at least one normal event;

further comprising code executable by at least one processor, the code including instructions for activating the at least one physiological sensor based on identification of the at least one abnormal event, to confirm or retract the at least one abnormal event, to reduce overall power consumption.

8. The system of claim 7, wherein:

the at least one activity sensor is further configured to sense at least one of: at least one gesture and at least one postural data of the subject within the space; and the monitoring unit is further configured to receive at least one of the at least one gesture and the at least one postural change; and generate, based on a contextual analysis of a correlation of the body movement and the location and time of day and day of week with at least one of the at least one gesture and the at least one postural change, a message indicative of at least one abnormal event or at least one normal event.

9. A system for detection and monitoring of at least one position based activity by a subject, comprising:

a wearable monitoring device configured to be detachable and wearable on a subject, comprising:

at least one position tag configured to communicate with a plurality of anchor devices, each device including at least one sensor configured for tracking location of the at least one position tag in a space, and at least one activity sensor configured to sense at least one body movement of the subject within the space; and a monitoring unit configured to:

receive body movement and location data of the subject within the space, and a time of day, and day of week;

generate, based on a contextual analysis of a deviation of a correlation of the body movement and the location data and time of day and day of week from past recorded data of a previous combination of similar body movement data and location data and time of day and day of week, a message indicative of at least one abnormal event or at least one normal event; and an activity database storing learned data representing combinations of tracked subject location data and subject body movement data and/or gesture data and/or physiological data, correlated with time of day and day of week, representing different activities, wherein the activity database is in communication with the monitoring unit, and the monitoring unit uses the activity database to identify the at least one abnormal event, wherein the data within the activity database is collected based on one or more members of the group consisting of: past data of the same subject, data from other similar subjects, data from other similar subjects having similar medical conditions as the subject;

wherein the monitoring unit is further configured to at least one of: dynamically increase the rate at which messages are transmitted by the at least one activity sensor of the wearable device when the at least one abnormal event is detected to improve accuracy of determination of the position of the subject, and dynamically reduce the rate at which messages are transmitted when the at least one normal event is detected to reduce overall power consumption.

10. The system of claim 9, wherein the wearable monitoring device further includes a global position element configured to generate a global location of the data representing at least one tracked location of the subject when the subject is located out outdoors and out of range of the plurality of anchor devices.

11. The system of claim 9, wherein at least one of the plurality of anchor devices includes an audio monitor used for communication between the subject and a caregiver based on the identification of the at least one abnormal event.

12. The system of claim 9, wherein the monitoring unit is further configured to detect a fall based on the detected deviation from past routine in at least one of the following: the subject is static for a predefined period of time in a location in which the subject is usually active, the subject is static in an abnormal location for the current time of day, the subject is in a location where the subject is usually active and with abnormal heart-rate.

13. A computerized method of detection and monitoring of care provided by a caregiver to a subject, comprising:

providing a wearable monitoring device including at least one position tag to a caregiver, and another wearable monitoring device including at least one position tag to a subject, the at least one position tag configured to communicate with plurality of anchor devices, each device including at least one sensor for tracking location of the position tag in a space, each wearable monitoring device further configured to be detachable and wearable on the caregiver and on the subject being cared for by the caregiver;

calculating a quality of care dataset based on the relative tracked locations of the at least one position tag of the subject relative to the at least one position tag of the caregiver;

analyzing the quality of care dataset to identify at least one abnormal event in care provided to the subject by the caregiver;

generating an alert indicative of the at least one abnormal event;

providing at least one activity sensor to the caregiver and to the subject, the at least one activity sensor configured to sense at least one of a posture and a gesture of the caregiver and at least one of a posture and a gesture of the subject;

identifying at least one of a sequence of gestures and a sequence of postures of at least one of the caregiver and the subject representing good care or bad care; and calculating the quality of care dataset based on the sequence of gestures;

wherein identifying at least one of the sequence of gestures and sequence of postures is based on machine learning including training data gathered from the same caregiver and/or different caregivers performing predefined good care or bad care on the same subject and/or different subjects.

14. The method of claim 13, wherein the quality of care data set includes at least one quality of care metric calculated based on one or more members of the group consisting of: an average of a distance between the caregiver and the subject as a function of time, a maximal of the distance, and a function of the distance over time.

15. The method of claim 13, wherein analyzing further comprising analyzing the quality of care dataset based on a location context of the subject and the caregiver based on body movements detected by respective position tags.

16. The method of claim 13, wherein the quality of care dataset is calculated based on an analysis of voice data generated by the subject calling the caregiver, and the responsiveness of the caregiver to the calling subject associated with changes in the relative locations of the at least one position tag of the subject relative to the at least one position tag of the caregiver.

* * * * *